(12) United States Patent
Van Heugten et al.

(10) Patent No.: US 11,007,051 B2
(45) Date of Patent: *May 18, 2021

(54) SYSTEMS, DEVICES, AND/OR METHODS FOR MANAGING IMPLANTABLE DEVICES

(71) Applicant: e-Vision Smart Optics, Inc., Sarastoa, FL (US)

(72) Inventors: Anthony Van Heugten, Sarasota, FL (US); Joel Zychick, Bethpage, NY (US)

(73) Assignee: e-Vision Smart Optics, Inc., Sarasota, FL (US)

(*) Notice: Subject to any disclaimer, the term of this patent is extended or adjusted under 35 U.S.C. 154(b) by 123 days.

This patent is subject to a terminal disclaimer.

(21) Appl. No.: 16/275,673

(22) Filed: Feb. 14, 2019

(65) Prior Publication Data

US 2019/0175334 A1 Jun. 13, 2019

Related U.S. Application Data

(60) Division of application No. 15/875,225, filed on Jan. 19, 2018, now Pat. No. 10,695,167, which is a (Continued)

(30) Foreign Application Priority Data

Apr. 17, 2013 (GB) ..................... 1306971

(51) Int. Cl.
*A61F 2/16* (2006.01)
*A61F 2/14* (2006.01)

(52) U.S. Cl.
CPC ............. *A61F 2/1624* (2013.01); *A61F 2/14* (2013.01)

(58) Field of Classification Search
None
See application file for complete search history.

(56) References Cited

U.S. PATENT DOCUMENTS

2003/0210377 A1* 11/2003 Blum .................... G02C 7/101
351/159.4
2006/0095128 A1* 5/2006 Blum .................... G06F 1/163
623/6.37

(Continued)

FOREIGN PATENT DOCUMENTS

CN 101094626 12/2007
CN 101646400 2/2010

(Continued)

OTHER PUBLICATIONS

Lu, "Piezoelectric Nanogenerator Using p-Type ZnO Nanowire Arrays", Jan. 13, 2009, 5 page(s), Nano Letters, 2009, 9(3)-pp. 1223-1227.

*Primary Examiner* — Leslie Lopez
(74) *Attorney, Agent, or Firm* — Michael Haynes PLC; Michael N. Haynes

(57) ABSTRACT

Certain exemplary embodiments can provide a system, machine, device, manufacture, circuit, composition of matter, and/or user interface adapted for and/or resulting from, and/or a method and/or machine-readable medium comprising machine-implementable instructions for, activities that can comprise and/or relate to, via a device implanted in a mammal, sensing a ciliary muscle movement and/or force and/or converting the ciliary muscle movement and/or force to a signal and/or a predetermined form of power.

5 Claims, 5 Drawing Sheets

Related U.S. Application Data continuation of application No. 13/866,262, filed on Apr. 19, 2013, now abandoned.

(60) Provisional application No. 61/636,969, filed on Apr. 23, 2012.

(56) References Cited

U.S. PATENT DOCUMENTS

| | | |
|---|---|---|
| 2006/0122531 A1 | 6/2006 | Goodall |
| 2007/0088433 A1 | 4/2007 | Esch |
| 2008/0136775 A1 | 6/2008 | Conant |
| 2008/0208335 A1 | 8/2008 | Blum |
| 2009/0204210 A1 | 8/2009 | Pynson |
| 2009/0264966 A1 | 10/2009 | Blum |
| 2010/0110372 A1 | 5/2010 | Pugh |
| 2010/0228346 A1 | 9/2010 | Esch |
| 2010/0331977 A1 | 12/2010 | Schaper, Jr. |
| 2011/0040376 A1 | 2/2011 | Christie |
| 2012/0078224 A1* | 3/2012 | Lerner .................. A61F 9/0017 604/506 |
| 2012/0140167 A1 | 6/2012 | Blum |
| 2013/0041235 A1 | 2/2013 | Rogers |
| 2013/0238090 A1 | 9/2013 | Pugh |

FOREIGN PATENT DOCUMENTS

| | | |
|---|---|---|
| CN | 101795642 | 8/2010 |
| EP | 2620802 | 7/2013 |
| JP | 2006518222 | 8/2006 |
| JP | 2008543350 | 12/2008 |
| JP | 2009516570 | 4/2009 |
| JP | 2010517639 | 5/2010 |
| JP | 20100522443 | 7/2010 |
| WO | WO/04/0544471 | 7/2004 |
| WO | WO07/061688 | 5/2007 |
| WO | WO07051171 | 5/2007 |
| WO | WO08001859 | 7/2008 |
| WO | WO/08097915 | 8/2008 |
| WO | WO08/143720 | 11/2008 |
| WO | WO10/151757 | 12/2010 |
| WO | WO 2011/020078 | 2/2011 |
| WO | WO2011153158 | 12/2011 |
| WO | WO12006691 | 1/2012 |

* cited by examiner

SYSTEMS, DEVICES, AND/OR METHODS FOR MANAGING IMPLANTABLE DEVICES

CROSS-REFERENCES TO RELATED APPLICATIONS

This application claims priority to, and incorporates by reference herein in its entirety, U.S. Provisional Patent Application 61/636,969, filed 23 Apr. 2012 and pending United Kingdom Patent Application 1306971.1, filed 17 Apr. 2013.

BRIEF DESCRIPTION OF THE DRAWINGS

A wide variety of potential, feasible, and/or useful embodiments will be more readily understood through the herein-provided, non-limiting, non-exhaustive description of certain exemplary embodiments, with reference to the accompanying exemplary drawings in which.

DESCRIPTION

Figure 1:
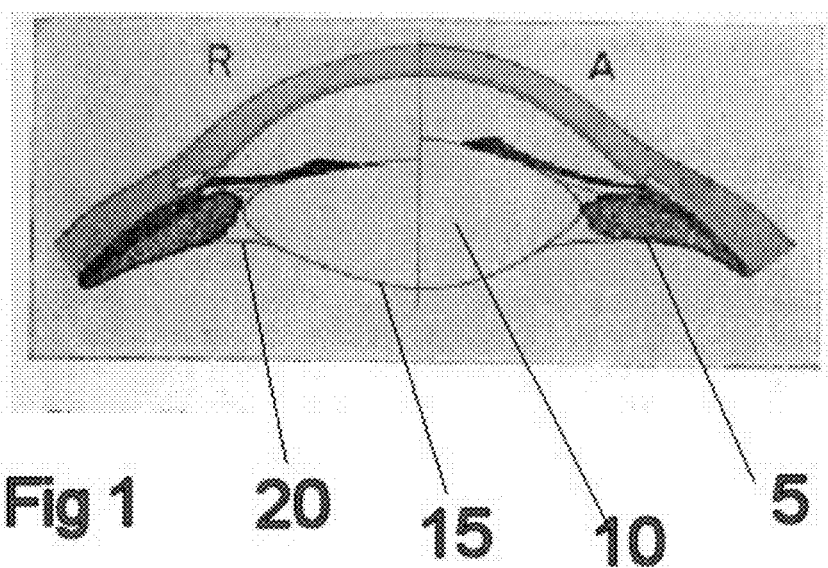
FIG. 1 is a side view of an exemplary lens of an exemplary mammalian eye.

Certain exemplary embodiments can provide a system, machine, device, manufacture, circuit, composition of matter, and/or user interface adapted for and/or resulting from, and/or a method and/or machine-readable medium comprising machine-implementable instructions for, activities that can comprise and/or relate to, via a device implanted in a mammal, sensing a ciliary muscle movement and/or force and/or converting the ciliary muscle movement and/or force to a signal and/or a predetermined form of power.

Certain exemplary embodiments can provide a system, machine, device, manufacture, circuit, composition of matter, and/or user interface adapted for and/or resulting from, and/or a method and/or machine-readable medium comprising machine-implementable instructions for, activities that can comprise and/or relate to:

from a first transmitter adapted to be operated by a predetermined first finger of a user:
wirelessly transmitting a first signal to one or more receivers of an ophthalmic device when the first transmitter is within a predetermined proximity of the one or more receivers, the first signal potentially adapted to cause the ophthalmic device to provide the user with a first predetermined visual condition; and/or from a second transmitter adapted to be operated by a predetermined second finger of the user:
wirelessly transmit a second signal to the one or more receivers when the second transmitter is within a predetermined proximity of the one or more receivers, the second signal potentially adapted to cause the ophthalmic device to provide the user with a second predetermined visual condition.

It is now feasible to implant into the human eye devices that require electrical power to operate. For example, it is now feasible to implant into the eye an optical lens that can change power to restore the accommodative capability of the eye. Such devices typically need electrical power to operate. Some such devices need a means by which they can be controlled to perform their intended function.

Certain exemplary embodiments can produce power inside of the eye so that the implantable device does not require external devices to operate. Certain exemplary embodiments can produce one or more usable signals to trigger and/or control the use of one or more implantable devices to achieve their purpose, such as an optical focusing lens.

Certain exemplary embodiments can harness the power of the ciliary muscle. When the human brain requires that the eye change focus, the ciliary muscle is commanded to actuate. This actuation can be used for power generation and/or for generating a signal to trigger a change in focus.

The cilary muscle is a ring-shaped muscle inside of the eye that is connected by strings, or zonules, to the lens of the eye. When the muscle actuates is becomes smaller in diameter, relaxing the pulling force on the zonules, allowing the lens to relax into a steeper-curved shape, producing more optical power. When the muscle relaxes, the ring shape expands, the zonules pull on the lens, and the lens becomes less curved with less optical power. This is the generally accepted theory of accommodation (i.e., Helmholtz), and will be the model used herein. However, there are competing theories being considered (e.g., Schachar), that propose that the accommodative action of the eye is caused by the reverse of this process. For purposes of this document, if the second theory of accommodation proves to be true, then the concepts described herein are still valid, except that the mechanisms will need to be adjusted to take into account the opposite forces being harnessed and/or monitored, and as such it will become apparent to the reader that those skilled in the art of mechanical engineering easily can adjust the design disclosed herein to accomplish this.

When a person forms a cataract in the lens of their eye, the lens might be replaced by a prosthetic lens referred to as an Intraocular Lens, or IOL. As known to those skilled in the art of ophthalmic cataract surgery, the capsule is opened up, the cataract lens is removed, and a new IOL is placed into the capsule to replace the cataract lens. After healing, the ciliary muscle continues to operate, i.e., contracting and expanding forces are created, but it has no effect upon the new IOL. A newer approach is to implant a very-low-power-consuming electro-active lens into the eye, and allow the lens to change optical power yet remain stationary.

Certain exemplary embodiments can place, adjacent to the ciliary muscle, a device that converts the mechanical forces created by the cilary muscle into power, and that power in turn is used to actuate a lens power change, or stored for later use, for example into a battery or capacitor. Certain exemplary embodiments of an implantable ciliary muscle power converter can create electrical power by physically moving a magnet within a coil to produce a potential, but other structures and/or principles are also useable to produce electrical power, and a non-limiting example would be the use of the compression of nanowires and/or a piezoelectric strip. Although certain exemplary embodiments can produce electrical power, other forms of power, such as hydraulic power and/or mechanical spring power, can be created and/or used.

Certain exemplary embodiments can monitor the production of power, and/or, from the appearance of this power being created, can interpret such power as a signal that accommodation is being needed. Certain exemplary embodiments can provide and/or utilize a variable resistor to sense movement of the ciliary muscle, but other methods also can be used, and non-limiting examples would be monitoring the power produced by power sensors attached to the power generators (e.g., voltage sensors, current sensors, proximity sensors, flow sensors, pressure sensors, strain gages, etc.), compression force sensors attached to the mechanisms or to the cilary muscle itself (e.g., voltage sensors, current sensors, proximity sensors, flow sensors, pressure sensors, strain gages, etc.), etc.

The power-harnessing and movement sensing device in contact with the ciliary muscle, such as attached to the capsular equator, also can be used as a mechanical platform upon which to attach the optical power changing device and/or its associated controls.

In certain exemplary embodiments, the power harnessing device and/or movement sensing device instead can be placed inside of the capsule, and/or in turn, the ciliary muscle action can be transferred to the device via the zonules connecting the capsule to the ciliary muscle.

FIG. 1 shows one theory of the mechanism of accommodation. On the side marked "A," ciliary muscle 5 is activated, becoming smaller in diameter, and lens 10 is most steep in curvature. Lens 10 is encapsulated in capsule 15, and is connected to ciliary muscle 5 via zonules 20. On side marked "R," ciliary muscle is relaxed, increasing in diameter such that zonules 20 pull on capsule 15, making lens 10 flatter, thus with less optical power.

Figure 2:
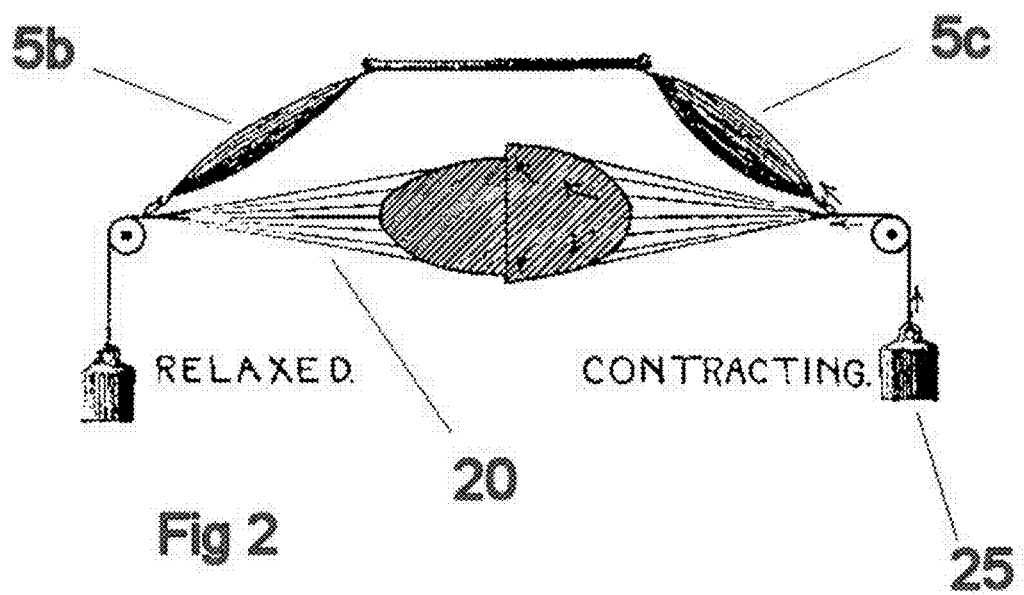
FIG. 2 is a block diagram of an exemplary embodiment of a system.

FIG. 2 shows schematically where the mechanical power can be created. When ciliary muscle 5b is relaxed, weight 25 is dropped, and when ciliary muscle 5c is activated, weight 25 is lifted.

Figure 3:
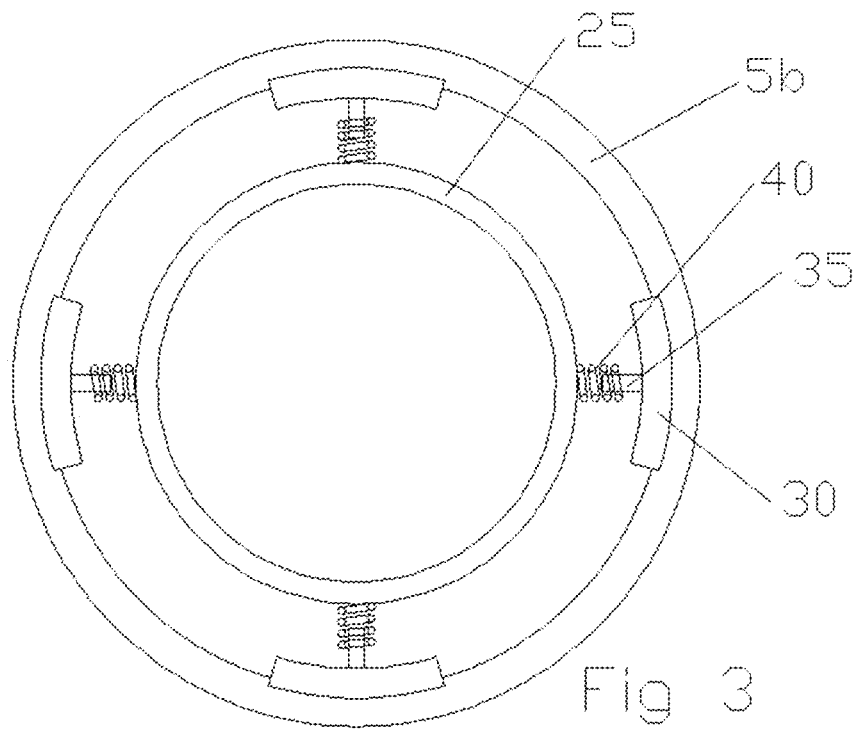
FIG. 3 is a block diagram of an exemplary embodiment of a system.
Figure 4:
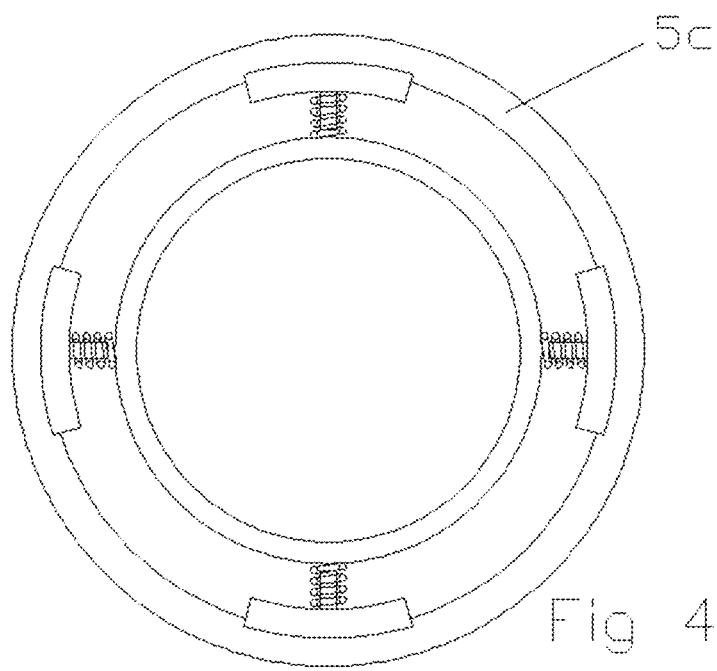
FIG. 4 is a block diagram of an exemplary embodiment of a system.

FIGS. 3 and 4 show an exemplary embodiment of harnessing the power of the ciliary muscle.

In FIG. 3, ciliary muscle 5b is relaxed in its largest diameter state. Support structures 30 are cradling ciliary muscle 5b, and have magnets 35 attached. Magnets 35 are surrounded in a slideable fashion by coils 40, which in turn are supported by ring 25.

In FIG. 4, ciliary muscle 5c can contract, becoming smaller in diameter, thereby moving magnets 35 deeper into coils 40 and creating an electrical potential that can be harnessed for battery and/or power cell recharging, and/or ciliary muscle monitoring. One or more of the combinations of magnet 35 and coil 40 can be replaced by a variable resistor, known to those skilled in the art of electronics, so that the variable resistor can be used to monitor the movement of the ciliary muscle. One or more combinations of magnet 35 and coil 40 can be replaced with nanowires such that the contraction of ciliary muscle 5c causes a pinching of a group of nanowires, which in turn can create an electrical potential. Also, as known to those skilled in the art of power generation, moving magnets relative to structures other than coils, even a single strand of wire, can create power. Also known to those skilled in the art of power generation, the mere bending, compressing, expanding or deflection of select materials can be used to create energy.

When it is required of the accommodating optic to perform the function of accommodation, a control signal of some type typically must be provided to initiate the process of changing the optical power. Although the contraction of the ciliary muscle can be monitored and/or interpreted to indicate the need for accommodation, then automatically detect and act upon such signals, it also can be desirable to provide the ability to manually control the accommodation through deliberate switching rather than automatic.

For example, a person might be in an environment where the light level changes frequently causing the pupil to open and close frequently. Although the pupil movement would be in response only to changing light levels and not demands for accommodation, an automatic system might be confused by such input, and trigger accommodation when it is not required. It may also be desirable to provide a simpler product without the complexity of an automatic accommodation system and provide only a manually controllable system to provide greater robustness, lower cost, and/or smaller size.

To meet the needs of a manually controlled optic, and/or allow a person to learn to adjust the focus of their vision in a more instinctive, habitual, and/or reflexive manner, it is proposed to attach two or more wireless transmitters onto and/or into two or more locations on and/or in the wearer's fingers and/or hands, and/or equip the implanted optic with a receiver or receivers to wirelessly communicate with the transmitters when the transmitters are within close and/or appropriate proximity to the receiver(s). Each transmitter can be programmed to send a unique signal calling for a particular action of the optic. For example, onto the index finger could be attached a transmitter with an instruction for the optic to "focus far." When the user wants to focus upon distant objects, they could bring their index finger near to their eye, triggering a "far focus" condition. A second transmitter could be attached to the long finger, and be programmed with the instruction "focus near." When the user wants to focus upon a near object, they could bring their long finger near to their eye, triggering a "near focus" condition. Combinations could be programmed so that if both fingers are brought simultaneously to the eye, alternative actions could be programmed into the optics to perform such things as "focus between far and near," or "turn off." By adding more transmitters to more fingers or other parts of the hand, more individual and even more combination instructions can be achieved. The transmitters can send a signal to a receiver inside of the eye. The receiver then can instruct an electro-active lens control circuit to adjust the lens to the optical power being signaled by the transmitter.

Having such a configuration of controllers attached to fingers and/or hands can allow the user to adapt to a very simple method to adjust their eyesight to various conditions, creating an environment for developing the skill to "act without thinking" when vision changes are required.

The technology for accomplishing the wireless communication exists in many forms, such as RFID circuits, which are generally known to those skilled in the art of radio telecommunications.

In another exemplary embodiment, for those unable or unwilling to use multiple fingers, a key-fob type of transmitter can be used. The transmitter can have multiple buttons and/or be programmed to transmit multiple instruction signals triggered by a sequence of button pushes.

In yet another exemplary embodiment, the transmitter can be the source of power to the implanted optic, either as the sole source, the primary source, or a supplementary source. When the transmitter is moved into close proximity of the eye, power can be transmitted into the optic via wireless transfer. Those skilled in the art of wireless power transmission can design such systems, with one exemplary method being inductance coils. Placing the transmitter close enough to the eye to transfer power could allow the power storage device inside the implant to recharge, and/or it could provide all the power required to trigger the optic without having an internal power storage device. Such a configuration can be used in an optic that utilizes a liquid crystal that changes optical state when power is applied, yet remains in that optical state when the power is removed, rather than reverting back to another "at rest state" when the power is removed.

Figure 5:
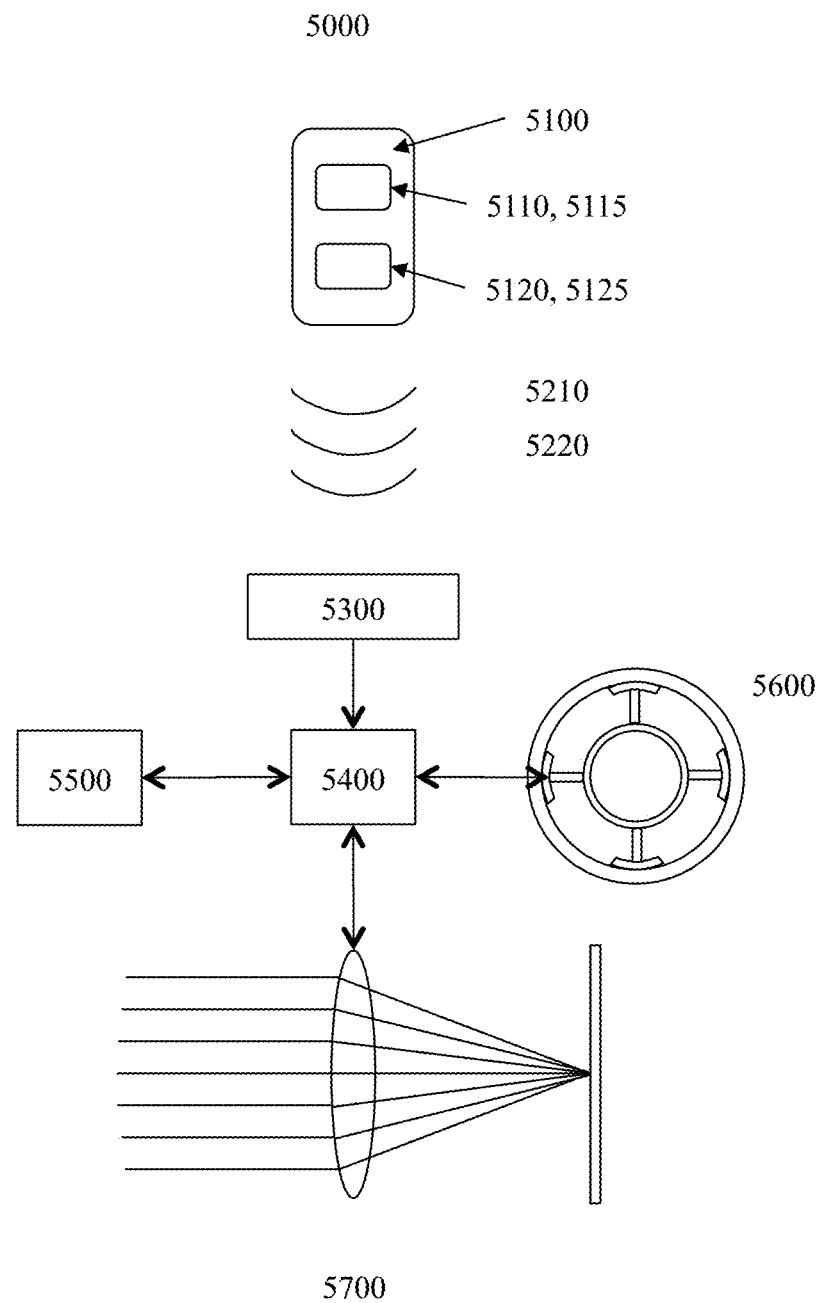
FIG. 5 is a block diagram of an exemplary embodiment of a system.

FIG. 5 is a block diagram of an exemplary embodiment of system 7000, which can comprise a carrier 5100 that can comprise any number of buttons, such as a first button 5110 and/or a second button 5120. First button 5110 can be actuated by a first predetermined finger of a user to cause a first transmitter 5115 to send a first wireless signal 5210 to receiver 5300, such as when first transmitter 5115 is within a predetermined proximity of receiver 5300. Second button 5120 can be actuated by a second predetermined finger of the user to cause second transmitter 5125 to send a second wireless signal 5220 to receiver 5300. Any additional buttons can function in a corresponding manner.

Carrier 5100, first transmitter 5110, and/or second transmitter 5120 can be adapted to be held in a hand of the user, worn by the user (e.g., as jewelry), worn on a predetermined finger (or other body part) of the user, and/or implanted into a predetermined finger (or other body part) of the user. For example, a transmitter or other related electronic circuit (such as a finger pressure sensor, a transmitter actuator, an antenna, a receiver, a controller, a battery, a power converter, etc.) can be skin-mounted on a finger, hand, arm, face, hip, thigh, temple, or elsewhere on a body via a flexible or stretchable substrate as described in US Patent Application Publication 20130041235, which, to the extent allowable by the law of the jurisdiction in which this application is filed, is incorporated herein by reference in its entirety.

Receiver 5300 can be worn by the user, worn on an eye of the user, and/or implanted in the user, such as inside the eye of the user. Receiver 5300 can be electrically connected to a controller 5400, which can be an information device as described herein, and/or which can be worn by the user, worn on an eye of the user, and/or implanted in the user, such as inside the eye of the user. Controller 5400 can be electrically connected to a power storage device 5500 (such as a battery), a ciliary muscle power converter 5600, and/or one or more ophthalmic devices 5700 (e.g., an electro-active lens), any of which can be worn by the user, worn on one or both eyes of the user, and/or implanted in the user, such as inside one or both eyes of the user.

Controller 5400 can be adapted to, upon receiving first signal 5210 via receiver 5300, cause ophthalmic device 5700 to adjust its optical power to provide the user with a first predetermined visual condition, such as a near field focus. Similarly, controller 5400 can be adapted to, upon receiving second signal 5220 via receiver 5300, cause ophthalmic device 5700 to adjust its optical power to provide the user with a second predetermined visual condition, such as a far field focus. Other visual conditions are possible, such as a predetermined optical power, focal distance, wavelength reception (e.g., infra-red, night vision, visual, rose-tinted, ultra-violet, etc.), polarity reception, astigmatic correction, spherical correction, aberration correction, and/or no correction, etc.

Controller 5400 can be adapted to cause power transmitted via signal 5210, 5220 and received by receiver 5300 to be stored via power storage device 5500 and/or utilized to operate on or more components of system 5000, such as ophthalmic device 5700.

Controller 5400 can be adapted to cause power received from ciliary muscle power converter 5600 to be stored via power storage device 5500 and/or be utilized, such as via itself, receiver 5300, and/or ophthalmic device 5700.

Figure 6:
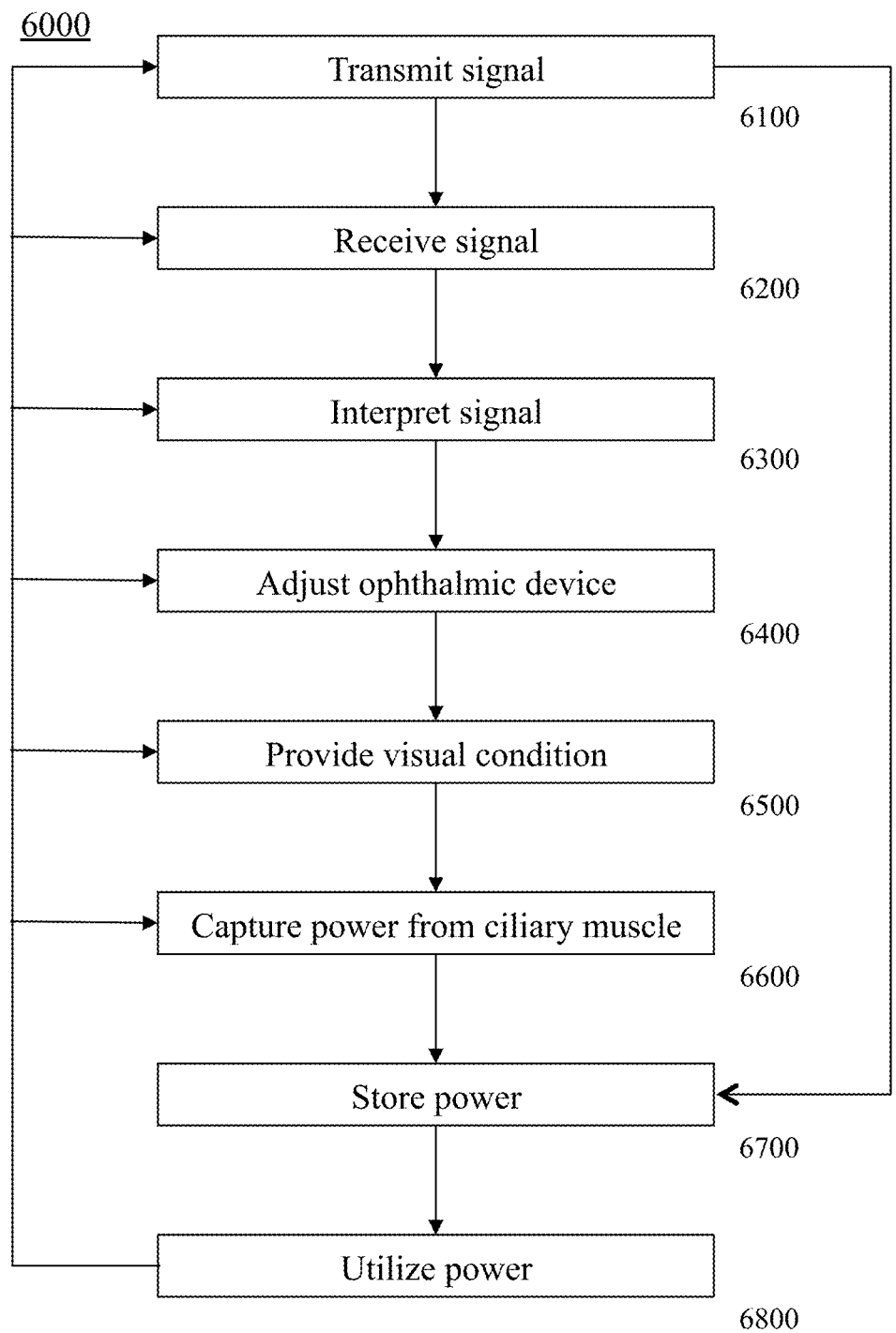
FIG. 6 is a flowchart of an exemplary embodiment of a method.

FIG. 6 is a flowchart of an exemplary embodiment of a method 6000. At activity 6100, a signal to be transmitted, such as responsive to a button being pressed or otherwise a transmitter being actuated. At activity 6200, the signal can be received, such as by a receiver. At activity 6300, the signal can interpreted, such as by the receiver and/or by a controller. At activity 6400, a ophthalmic device can be adjusted, such as responsive to the interpreted signal. At activity 6500, the one or more adjustments to the ophthalmic device can provide a visual condition to a wearer of the ophthalmic device.

At activity 6600, power generated by the ciliary muscle of the wearer, potentially responsive to a change in visual condition of the wearer, can be captured. At activity 6700, power can be stored, the power being, for example, power captured from the ciliary muscle and/or power captured from the transmitted signal. At activity 6800, the captured and/or stored power can be utilized, such as to power the transmitter, receiver, controller, ophthalmic device, and/or ciliary muscle power converter, etc.

Figure 7:
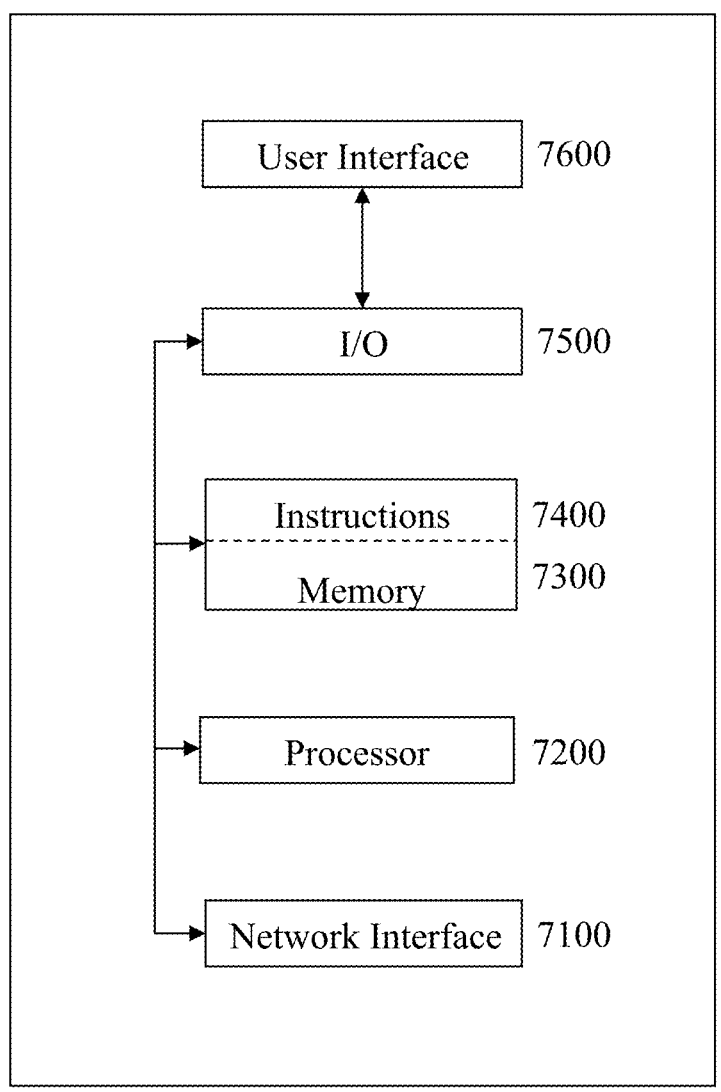
FIG. 7 is a block diagram of an exemplary embodiment of an information device.

FIG. 7 is a block diagram of an exemplary embodiment of an information device 7000, which in certain operative embodiments can be adapted to implement any algorithm described herein, such as those attributed to a converter, controller, transmitter, and/or receiver. Information device 7000 can comprise any of numerous transform circuits, which can be formed via any of numerous communicatively-, electrically-, magnetically-, optically-, fluidically-, mechanically-, chemically-, and/or biochemically-coupled physical components, such as for example, one or more network interfaces 7100, one or more processors 7200, one or more memories 7300 containing instructions 7400, one or more input/output (I/O) devices 7500, and/or one or more user interfaces 7600 coupled to I/O device 7500, etc.

In certain exemplary embodiments, via one or more user interfaces 7600, such as a graphical user interface, a user can view a rendering of information related to researching, designing, modeling, creating, developing, building, manufacturing, operating, maintaining, storing, marketing, selling, delivering, selecting, specifying, requesting, ordering, receiving, returning, rating, and/or recommending any of the products, services, methods, user interfaces, and/or information described herein. For example, one or more user interfaces 7600, a user can program, review, test, model, adjust, modify, update, enable, and/or disable instructions 7400, such as instructions to detect a button activation, transmit a signal, receive a signal, interpret a signal, adjust an ophthalmic device, interpret a state of an ophthalmic device, sense muscle movement and/or force, convert muscle movement and/or force to power (such as electrical power), capture power (such as from muscle and/or transmitted signal), store power, and/or utilize power.

Certain exemplary embodiments can provide a system, machine, device, manufacture, circuit, composition of matter, and/or user interface adapted for and/or resulting from, and/or a method and/or machine-readable medium comprising machine-implementable instructions for, activities that can comprise and/or relate to, a device comprising:
    an implantable ciliary muscle power converter adapted to connect to an eye structure and to convert mechanical forces generated by the ciliary muscle into power;
    wherein:
        the implantable ciliary muscle power converter comprises a magnet;

the implantable ciliary muscle power converter comprises a coil;
the implantable ciliary muscle power converter comprises a spring;
the implantable ciliary muscle power converter comprises a hydraulic piston;
the implantable ciliary muscle power converter comprises a hydraulic valve;
the implantable ciliary muscle power converter comprises a plurality of nanowires;
the implantable ciliary muscle power converter comprises a piezoelectric strip;
the implantable ciliary muscle power converter is adapted to attach to the ciliary muscle;
the implantable ciliary muscle power converter is attached to the capsular equator;
the implantable ciliary muscle power converter is adapted to attach to one or more zonules;
the implantable ciliary muscle power converter is adapted to be placed inside a capsule of the eye; and/or
a variable resistor adapted to sense movement of the ciliary muscle.

Certain exemplary embodiments can provide a system, machine, device, manufacture, circuit, composition of matter, and/or user interface adapted for and/or resulting from, and/or a method and/or machine-readable medium comprising machine-implementable instructions for, activities that can comprise and/or relate to, a device comprising:
an implantable ciliary muscle movement sensor;
wherein:
the implantable ciliary muscle movement sensor is adapted to attach to the ciliary muscle;
the implantable ciliary muscle movement sensor is adapted to attach to one or more zonules;
the implantable ciliary muscle movement sensor is adapted to be placed inside a capsule of the eye; and/or
the implantable ciliary muscle movement sensor is adapted to attach to a ciliary muscle power converter.

Certain exemplary embodiments can provide a system, machine, device, manufacture, circuit, composition of matter, and/or user interface adapted for and/or resulting from, and/or a method and/or machine-readable medium comprising machine-implementable instructions for, activities that can comprise and/or relate to:
via a device implanted in a mammal, converting a ciliary muscle force to predetermined form of power;
via a device implanted in a mammal, sensing a ciliary muscle movement; and/or
via a device implanted in a mammal, sensing a ciliary muscle force.

Certain exemplary embodiments can provide a system, machine, device, manufacture, circuit, composition of matter, and/or user interface adapted for and/or resulting from, and/or a method and/or machine-readable medium comprising machine-implementable instructions for, activities that can comprise and/or relate to, converting ciliary muscle force to electrical power and/or sense ciliary muscle movement.

Certain exemplary embodiments can provide a system, machine, device, manufacture, circuit, composition of matter, and/or user interface adapted for and/or resulting from, and/or a method and/or machine-readable medium comprising machine-implementable instructions for, activities that can comprise and/or relate to:
an electro-active lens implanted into a user's eye;
a control circuit adapted to control an optical power of the electro-active lens; and/or
a receiver adapted to receive signals from a transmitter that is adapted to send a predetermined signal to the receiver; the predetermined signal adapted to cause the receiver to adjust an optical power of the electro-active lens.

Certain exemplary embodiments can provide a system, machine, device, manufacture, circuit, composition of matter, and/or user interface adapted for and/or resulting from, and/or a method and/or machine-readable medium comprising machine-implementable instructions for, activities that can comprise and/or relate to:
a first transmitter adapted to:
be operated by a first finger of a user;
wirelessly transmit a first signal to one or more receivers of an ophthalmic device when the first transmitter is within a predetermined proximity of the one or more receivers, the ophthalmic device implanted in or worn by the user, the first signal adapted to cause the ophthalmic device to provide the user with a first predetermined visual condition;
a second transmitter adapted to:
be operated by a second finger of the user;
wirelessly transmit a second signal to the one or more receivers when the second transmitter is within a predetermined proximity of the one or more receivers, the second signal adapted to cause the ophthalmic device to provide the user with a second predetermined visual condition;
the receiver; and/or
the ophthalmic device;
wherein:
the receiver is implanted in the user;
the receiver is implanted inside an eye of the user;
the receiver is worn on an eye of the user;
the ophthalmic device is implanted inside an eye of the user;
the ophthalmic device is worn on an eye of the user;
the ophthalmic device comprises an electro-active lens;
the first transmitter is adapted to be implanted in the first finger;
the first transmitter is adapted to be worn on the first finger;
the first finger is predetermined and/or the second finger is predetermined;
the first transmitter is adapted to be held in a hand of the user;
the first transmitter and/or the second transmitter is integrated into a jewelry item;
the first transmitter comprises a button adapted to provoke transmission of the first signal;
the first transmitter is adapted to transfer electrical energy to an energy storage device of the ophthalmic device;
the first transmitter is adapted to transfer sufficient electrical energy to operate the ophthalmic device;
the first transmitter comprises one or more inductance coils;
the first signal identifies the first transmitter;
the first transmitter is adapted to control one or more liquid crystals of the ophthalmic device;
the first transmitter is adapted to change an optical state of one or more liquid crystals of the ophthalmic device;
the first visual condition is associated with two eyes of the user;

the first visual condition is associated with only one eye of the user;
the first visual condition is a focal distance;
the first visual condition is a far focal distance;
the first visual condition is a near focal distance;
the first visual condition is a changing focal distance;
the first visual condition is an optical power; and/or
the first visual condition is a lack of visual correction.

Certain exemplary embodiments can provide a system, machine, device, manufacture, circuit, composition of matter, and/or user interface adapted for and/or resulting from, and/or a method and/or machine-readable medium comprising machine-implementable instructions for, activities that can comprise and/or relate to:

from a first transmitter adapted to be operated by a predetermined first finger of a user:
  wirelessly transmitting a first signal to one or more receivers of an ophthalmic device when the first transmitter is within a predetermined proximity of the one or more receivers, the ophthalmic device implanted in or worn by the user, the first signal adapted to cause the ophthalmic device to provide the user with a first predetermined visual condition; and/or from a second transmitter adapted to be operated by a predetermined second finger of the user:
  wirelessly transmit a second signal to the one or more receivers when the second transmitter is within a predetermined proximity of the one or more receivers, the second signal adapted to cause the ophthalmic device to provide the user with a second predetermined visual condition.

Definitions

When the following terms are used substantively herein, the accompanying definitions apply. These terms and definitions are presented without prejudice, and, consistent with the application, the right to redefine these terms via amendment during the prosecution of this application or any application claiming priority hereto is reserved. For the purpose of interpreting a claim of any patent that claims priority hereto, each definition in that patent functions as a clear and unambiguous disavowal of the subject matter outside of that definition.

a—at least one.
aberration—one or more limitations and/or defects in an optical component, such as a lens and/or mirror, that is contacted by a plurality of light rays, such limitations and/or defects preventing the light rays from converging at one focus and potentially due to, e.g., the optical component comprising one or more surfaces that are not perfectly planar, such as one or more spherical surfaces.
acquire—to obtain, get, import, receive, and/or gain possession of.
across—from one side to another.
activity—an action, act, step, and/or process or portion thereof.
adapted to—suitable, fit, and/or capable of performing a specified function.
adapter—a device used to effect operative compatibility between different parts of one or more pieces of an apparatus or system.
adjust—to change so as to match, fit, adapt, conform, and/or be in a more effective state.
align—to adjust substantially into a proper orientation and/or location with respect to another thing.
and/or—either in conjunction with or in alternative to.
apparatus—an appliance or device for a particular purpose
associate—to join, connect together, and/or relate.
attach—to fasten, secure, couple, and/or join.
auto-focus—a system in a camera that automatically adjusts the lens so that the object being photographed is in focus, often using a time delay associated with reflecting infrared light off of the object to estimate the distance of the object from the camera.
automatic—performed via an information device in a manner essentially independent of influence and/or control by a user. For example, an automatic light switch can turn on upon "seeing" a person in its "view", without the person manually operating the light switch.
be—to exist in actuality.
beam of light—a projection of light radiating from a source.
Boolean logic—a complete system for logical operations.
border—to be located and/or positioned adjacent to an outer edge, surface, and/or extent of an object.
bound—(n) a boundary, limit, and/or further extent of; (v) to limit an extent.
bus—an electrical conductor that makes a common connection between a plurality of circuits.
button—a protuberant part, a small finger-actuated surface comprised by a mechanism that completes an electric circuit when pushed, such as one that operates a doorbell and/or machine and/or, in graphical user interface systems, a well-defined area within the interface that is clicked to select a command.
by—via and/or with the use and/or help of.
camera—a device often comprising a lightproof enclosure having an aperture with a lens through which a still and/or moving image of an object is focused and recorded on a photosensitive film, plate, tape, and/or or sensor coupled to an electronic and/or optical memory device (e.g., RAM, EEPROM, flash memory, magnetic disk, optical disk, etc.).
can—is capable of, in at least some embodiments.
capsule—a cover or envelope partly or wholly surrounding a structure.
capture—to sense, receive, obtain, enter, store, and/or record information and/or data in memory.
cause—to bring about, provoke, precipitate, produce, elicit, be the reason for, result in, and/or effect.
change—(v.) to cause to be different; (n.) the act, process, and/or result of altering or modifying.
ciliary—relating to the ciliary body and associated structures of the eye.
circuit—a physical system comprising, depending on context: an electrically conductive pathway, an information transmission mechanism, and/or a communications connection, the pathway, mechanism, and/or connection established via a switching device (such as a switch, relay, transistor, and/or logic gate, etc.); and/or an electrically conductive pathway, an information transmission mechanism, and/or a communications connection, the pathway, mechanism, and/or connection established across two or more switching devices comprised by a network and between corresponding end systems connected to, but not comprised by the network.
co-operate—to work, act, and/or function together and/or in harmony, as opposed to separately and/or in competition.
coil—(n) a continuous loop comprising two or more turns of electrically conductive material; and/or a conductor that creates a magnetic field due to the flow of current therein; (v) to roll and/or form into a configuration having a substantially spiraled cross-section.

comprises—includes, but is not limited to, what follows.

comprising—including but not limited to.

concentric—having a common central axis.

condition—and existing circumstance and/or state at a particular time.

conductor—an electrically conductive material and/or component adapted to apply a voltage to an electro-active material.

configure—to make suitable or fit for a specific use or situation.

connect—to join or fasten together.

connect—to join or fasten together.

contact—to physically touch and/or come together.

containing—including but not limited to.

contiguous—neighboring and/or adjacent.

contrast—the difference in brightness between the light and dark areas of an image, such as a photograph and/or video image.

control—(n) a mechanical and/or electronic device used to operate a machine within predetermined limits; (v) to exercise authoritative and/or dominating influence over, cause to act in a predetermined manner, direct, adjust to a requirement, and/or regulate.

controller—a device and/or set of machine-readable instructions for performing one or more predetermined and/or user-defined tasks. A controller can comprise any one or a combination of hardware, firmware, and/or software. A controller can utilize mechanical, pneumatic, hydraulic, electrical, magnetic, optical, informational, chemical, and/or biological principles, signals, and/or inputs to perform the task(s). In certain embodiments, a controller can act upon information by manipulating, analyzing, modifying, converting, transmitting the information for use by an executable procedure and/or an information device, and/or routing the information to an output device. A controller can be a central processing unit, a local controller, a remote controller, parallel controllers, and/or distributed controllers, etc. The controller can be a general-purpose microcontroller, such the Pentium IV series of microprocessor manufactured by the Intel Corporation of Santa Clara, Calif., and/or the HCO8 series from Motorola of Schaumburg, Ill. In another embodiment, the controller can be an Application Specific Integrated Circuit (ASIC) or a Field Programmable Gate Array (FPGA) that has been designed to implement in its hardware and/or firmware at least a part of an embodiment disclosed herein.

convert—to transform, adapt, and/or change.

converter—a device that transforms, adapts, and/or changes.

correction—a change to a more desired value.

corresponding—related, associated, accompanying, similar in purpose and/or position, conforming in every respect, and/or equivalent and/or agreeing in amount, quantity, magnitude, quality, and/or degree.

couple—to join, connect, and/or link by any known approach, including mechanical, fluidic, acoustic, electrical, magnetic, and/or optical, etc. approaches.

coupleable—capable of being joined, connected, and/or linked together.

coupling—linking in some fashion.

create—to bring into being.

data—distinct pieces of information, usually formatted in a special or predetermined way and/or organized to express concepts, and/or represented in a form suitable for processing by an information device.

data structure—an organization of a collection of data that allows the data to be manipulated effectively and/or a logical relationship among data elements that is designed to support specific data manipulation functions. A data structure can comprise meta data to describe the properties of the data structure. Examples of data structures can include: array, dictionary, graph, hash, heap, linked list, matrix, object, queue, ring, stack, tree, and/or vector.

define—to establish the outline, form, and/or structure of deposit—to put, lay, place, position, and/or set down; and/or to fasten, fix, and/or secure.

determine—to find out, obtain, calculate, decide, deduce, ascertain, and/or come to a decision, typically by investigation, reasoning, and/or calculation.

device—a machine, manufacture, and/or collection thereof.

diffraction—the bending of a light ray in passing an edge formed by contiguous opaque and transparent edges.

digital—non-analog and/or discrete.

distance—a measure of physical separation.

diverge—to go or extend in different directions from a common point.

edge—a periphery, border, and/or boundary.

electric—powered by electricity.

electrical—relating to producing, distributing, and/or operating by electricity.

electrical energy—energy characterized by, and/or adapted to cause, a flow of electric charge through a conductor.

electrically—of, relating to, producing, or operated by electricity.

electrically coupled—connected in a manner adapted to allow a flow of electricity therebetween.

electro-active—a branch of technology concerning the interaction between various properties and electrical and/or electronic states of materials and/or involving components, devices, systems, and/or processes that operate by modifying the certain properties of a material by applying to it an electrical and/or magnetic field. Sub-branches of this technology include, but are not limited to, electro-optics.

electro-active element—a component that utilizes an electro-active effect, such as an electro-active filter, reflector, lens, shutter, liquid crystal retarder, active (i.e., non-passive) polarity filter, electro-active element that is movable via an electro-active actuator, and/or conventional lens movable by an electro-active actuator.

electro-optic—a branch of technology concerning the interaction between the electromagnetic (optical) and the electrical (electronic) states of materials and/or involving components, devices, systems, and/or processes that operate by modifying the optical properties of a material by applying to it an electrical field.

electrode—an electrically conducting element that emits and/or collects electrons and/or ions and/or controls their movement by means of an electric field applied to it.

emanate—to emit, radiate, and/or shine.

energy—usable heat or power, and/or the capacity of a body and/or system to do work, and/or a measurable physical quantity, with dimensions equivalent and/or convertible to mass times velocity squared, that is conserved for an isolated system.

equator—a circle dividing a sphere or other surface into congruent and/or two equal symmetrical parts.

estimate—(n) a calculated value approximating an actual value; (v) to calculate and/or determine approximately and/or tentatively.

etch—to wear away the surface of material (such as a metal, glass, etc.) by chemical action, such as the action of an acid.

eye—an organ of vision and/or light sensitivity; and/or either of a pair of hollow structures located in bony sockets of the skull, functioning together or independently, each having a lens capable of focusing incident light on an internal photosensitive retina from which nerve impulses are sent to the brain.

far—a CTO distance of at least approximately 3 or more meters.

field—a region of space characterized by a physical property, such as gravitational or electromagnetic force or fluid pressure, having a determinable value at every point in the region.

field of view—a range of space over which a camera can obtain an image and/or the angle between two rays passing through the perspective center (rear nodal point) of a camera lens to the two opposite sides of the format.

finger—any of the digits of the hand, sometimes excluding the thumb.

first—an initial entity in an ordering.

flat—having a substantially planar major face and/or having a relatively broad surface in relation to thickness or depth.

focus—to cause energy and/or light to concentrate and/or converge.

force—a capacity to do work or cause physical change; and/or an energy exerted upon, brought to bear, and/or the cause of motion and/or change in motion and/or a state of rest.

form—to produce, make, create, generate, construct, and/or shape.

Fresnel lens—a thin optical lens comprising concentric rings of segmental lenses.

from—used to indicate a source.

further—in addition.

generate—to create, produce, give rise to, and/or bring into existence.

gradient—a rate of change with respect to distance of a variable quantity.

grid—a network of lines, real or conceptual, that cross each other to form a series of regular shapes.

hand—the terminal part of the human arm located below the forearm, used for grasping and holding and typically comprising a wrist, palm, four fingers, and an opposable thumb.

haptic—involving the human sense of kinesthetic movement and/or the human sense of touch. Among the many potential haptic experiences are numerous sensations, body-positional differences in sensations, and time-based changes in sensations that are perceived at least partially in non-visual, non-audible, and non-olfactory manners, including the experiences of tactile touch (being touched), active touch, grasping, pressure, friction, traction, slip, stretch, force, torque, impact, puncture, vibration, motion, acceleration, jerk, pulse, orientation, limb position, gravity, texture, gap, recess, viscosity, pain, itch, moisture, temperature, thermal conductivity, and thermal capacity.

having—including but not limited to.

hold—to grip, and/or to have and/or keep within one's grasp.

human-machine interface—hardware and/or software adapted to render information to a user and/or receive information from the user; and/or a user interface.

hydraulic—of, involving, moved by, and/or operated by a fluid under pressure.

identify—to specify, recognize, detect, and/or establish the identity, origin, nature, and/or definitive characteristics of.

illuminate—to provide and/or brighten with light.

image—an at least two-dimensional representation of an object, entity, and/or phenomenon. Multiple images can be presented in a predetermined and timed sequence to recreate and/or produce an appearance of movement.

impinge—to collide and/or strike.

implant—to insert or embed (an object or a device) surgically.

including—including but not limited to.

index of refraction—a measure of the extent to which a substance slows down light waves passing through it. The index of refraction of a substance is equal to the ratio of the velocity of light in a vacuum to its speed in that substance. Its value determines the extent to which light is refracted when entering or leaving the substance.

indium tin oxide—a solid solution of indium(III) oxide ($In_2O_3$) and tin(IV) oxide ($SnO_2$), typically 90% $In_2O_3$, 10% $SnO_2$ by weight, that is typically transparent and colorless in thin layers and can serve as a metal-like mirror in the infrared region of the electromagnetic spectrum. It is a widely used transparent conducting oxide due to its electrical conductivity and optical transparency. Thin films of indium tin oxide are most commonly deposited on surfaces by electron beam evaporation, physical vapor deposition, and/or a range of sputter deposition techniques.

individually—of or relating to a distinct entity.

inductance—that property of an electrical circuit, and/or of two or more neighboring circuits, by which a varying current produces and/or induces an electromotive force in the circuit and/or neighboring circuits.

information device—any device capable of processing data and/or information, such as any general purpose and/or special purpose computer, such as a personal computer, workstation, server, minicomputer, mainframe, supercomputer, computer terminal, laptop, wearable computer, and/or Personal Digital Assistant (PDA), mobile terminal, Bluetooth device, communicator, "smart" phone (such as an iPhone-like and/or Treo-like device), messaging service (e.g., Blackberry) receiver, pager, facsimile, cellular telephone, a traditional telephone, telephonic device, a programmed microprocessor or microcontroller and/or peripheral integrated circuit elements, an ASIC or other integrated circuit, a hardware electronic logic circuit such as a discrete element circuit, and/or a programmable logic device such as a PLD, PLA, FPGA, or PAL, or the like, etc. In general any device on which resides a finite state machine capable of implementing at least a portion of a method, structure, and/or or graphical user interface described herein may be used as an information device. An information device can comprise components such as one or more network interfaces, one or more processors, one or more memories containing instructions, and/or one or more input/output (I/O) devices, one or more user interfaces coupled to an I/O device, etc.

information device—any device capable of processing data and/or information, such as any general purpose and/or special purpose computer, such as a personal computer, workstation, server, minicomputer, mainframe, supercomputer, computer terminal, laptop, wearable computer, and/or Personal Digital Assistant (PDA), mobile terminal, Bluetooth device, communicator, "smart" phone (such as an iPhone-like and/or Treo-like device), messaging service (e.g., Blackberry) receiver, pager, facsimile, cellular telephone, a traditional telephone, telephonic device, a programmed microprocessor or microcontroller and/or peripheral integrated circuit elements, an ASIC or other integrated circuit, a hardware electronic logic circuit such as a discrete element circuit, and/or a programmable logic device such as a PLD, PLA, FPGA, or PAL, or the like, etc. In general any device on which resides a finite state machine capable of implementing at least a portion of a method, structure, and/or or graphical user interface described herein may be used as an information device. An information device can comprise components such as one or more network interfaces, one or more processors, one or more memories containing instructions, and/or one or more input/output (I/O) devices, one or more user interfaces coupled to an I/O device, etc.

initialize—to prepare something for use and/or some future event.

input/output (I/O) device—any device adapted to provide input to, and/or receive output from, an information device. Examples can include an audio, visual, haptic, olfactory, and/or taste-oriented device, including, for example, a monitor, display, projector, overhead display, keyboard, keypad, mouse, trackball, joystick, gamepad, wheel, touchpad, touch panel, pointing device, microphone, speaker, video camera, camera, scanner, printer, switch, relay, haptic device, vibrator, tactile simulator, and/or tactile pad, potentially including a port to which an I/O device can be attached or connected.

inside—within a predetermined boundary.

install—to connect or set in position and prepare for use.

instructions—directions, which can be implemented as hardware, firmware, and/or software, the directions adapted to perform a particular operation and/or function via creation and/or maintenance of a predetermined physical circuit.

insulating—having a substantial resistance to the flow of electrical current.

integrated—formed and/or united into a whole and/or into another entity.

into—to a condition, state, or form of

IOL haptic—a structure that is part of an IOL and adapted to provide support for the IOL within the eye, generally to also provide centration of the optics of the IOL to the optical axis of the eye.

item—a single article of a plurality of articles and/or anything that can be at least partially, protected, housed, transported, concealed, supported, carried, and/or enclosed, etc., by a container.

jewelry—one or more objects of personal adornment, such as necklaces, pendants, chokers, collars, beads, brooches, amulets, medals, lapel pins, tie tacks, earrings, piercings, hair clips, head bands, rings, bracelets, bangles, watches, cuff links, bling, belts, and/or buckles, etc., and possibly including items such as iPods, smart phones, smart watches, headphones, pens, pencils, whistles, medical alert bracelets, dog tags, etc.

lack—a particular deficiency and/or absence.

layer—a continuous and relatively thin material, region, stratum, course, lamina, coating, and/or sheet having one or more functions. Need not have a constant thickness.

lens—a piece of transparent substance, often glass and/or plastic, having two opposite surfaces either both curved or one curved and one plane, used in an optical device for changing the convergence and/or focal point of light rays; and/or an optical device that transmits light and is adapted to cause the light to refract, concentrate, and/or diverge. A lens can be an ophthalmic lens, such as a spectacle lens, an intra ocular lens, and/or a contact lens.

light—electromagnetic radiation having a wavelength within a range of approximately 300 nanometers to approximately 1000 nanometers, including any and all values and subranges therebetween, such as from approximately 400 to approximately 700 nm, from the near infrared through the long wavelength, far infrared, and/or from the ultraviolet to X-rays and/or gamma rays.

light source—a device adapted to emit light responsive to an applied electrical current.

liquid—a body of matter that exhibits a characteristic readiness to flow, little or no tendency to disperse, and relatively high incompressibility, including pumpable and/or flowable slurries and/or suspensions.

liquid crystal—any of various liquids in which the atoms or molecules are regularly arrayed in either one dimension or two dimensions, the order giving rise to optical properties, such as anisotropic scattering, associated with the crystals.

locate—to place, set, find, and/or situate in a particular spot, region, and/or position.

logic gate—a physical device adapted to perform a logical operation on one or more logic inputs and to produce a single logic output, which is manifested physically. Because the output is also a logic-level value, an output of one logic gate can connect to the input of one or more other logic gates, and via such combinations, complex operations can be performed. The logic normally performed is Boolean logic and is most commonly found in digital circuits. The most common implementations of logic gates are based on electronics using resistors, transistors, and/or diodes, and such implementations often appear in large arrays in the form of integrated circuits (a.k.a., IC's, microcircuits, microchips, silicon chips, and/or chips). It is possible, however, to create logic gates that operate based on vacuum tubes, electromagnetics (e.g., relays), mechanics (e.g., gears), fluidics, optics, chemical reactions, and/or DNA, including on a molecular scale. Each electronically-implemented logic gate typically has two inputs and one output, each having a logic level or state typically physically represented by a voltage. At any given moment, every terminal is in one of the two binary logic states ("false" (a.k.a., "low" or "0") or "true" (a.k.a., "high" or "1"), represented by different voltage levels, yet the logic state of a terminal can, and generally does, change often, as the circuit processes data. Thus, each electronic logic gate typically requires power so that it can source and/or sink currents to achieve the correct output voltage. Typically, machine-implementable instructions are ultimately encoded into binary values of "0"s and/or "1"s and, are typically written into and/or onto a memory device, such as a "register", which records the binary value as a change in a physical property of the memory device, such as a change in voltage, current, charge, phase, pressure, weight, height, tension, level, gap, position, velocity, momentum, force, temperature, polarity, magnetic field, magnetic force, magnetic orientation, reflectivity, molecular linkage, molecular weight, etc. An exemplary register might store a value of "01101100", which encodes a total of 8 "bits" (one byte), where each value of either "0" or "1" is called a "bit" (and 8 bits are collectively called a "byte"). Note that because a binary bit can only have one of two different values (either "0" or "1"), any physical medium capable of switching between two saturated states can be used to represent a bit. Therefore, any physical system capable of representing binary bits is able to represent numerical quantities, and potentially can manipulate those numbers via particular encoded machine-implementable instructions. This is one of the basic concepts underlying digital computing. At the register and/or gate level, a computer does not treat these "0"s and "1"s as numbers per se, but typically as voltage levels (in the case of an electronically-implemented computer), for example, a high voltage of approximately +3 volts might represent a "1" or "logical true" and a low voltage of approximately 0 volts might represent a "0" or "logical false" (or vice versa, depending on how the circuitry is designed). These high and low voltages (or other physical properties, depending on the nature of the implementation) are typically fed into a series of logic gates, which in turn, through the correct logic design, produce the physical and logical results specified by the particular encoded machine-implementable instructions. For example, if the encoding request a calculation, the logic gates might add the first two bits of the encoding together, produce a result "1" ("0"+"1"="1"), and then write this result into another register for subsequent retrieval and reading. Or, if the encoding is a request for some kind of service, the logic gates might in turn access or write into some other registers which would in turn trigger other logic gates to initiate the requested service.

logical—a conceptual representation.

machine-implementable instructions—directions adapted to cause a machine, such as an information device, to perform one or more particular activities, operations, and/or functions via forming a particular physical circuit. The directions, which can sometimes form an entity called a "processor", "kernel", "operating system", "program", "application", "utility", "subroutine", "script", "macro", "file", "project", "module", "library", "class", and/or "object", etc., can be embodied and/or encoded as machine code, source code, object code, compiled code, assembled code, interpretable code, and/or executable code, etc., in hardware, firmware, and/or software.

machine-readable medium—a physical structure from which a machine, such as an information device, computer, microprocessor, and/or controller, etc., can store and/or obtain one or more machine-implementable instructions, data, and/or information. Examples include a memory device, punch card, player-piano scroll, etc.

magnet—an object that is surrounded by a magnetic field and that has the property, either natural or induced, of attracting iron and/or steel.

mammal—any of various warm-blooded vertebrate animals of the class Mammalia, including humans, characterized by a covering of hair on the skin and, in the female, milk-producing mammary glands for nourishing the young.

match—to mirror, resemble, harmonize, fit, correspond, and/or determine a correspondence between, two or more values, entities, and/or groups of entities.

material—a substance and/or composition.

may—is allowed and/or permitted to, in at least some embodiments.

memory device—an apparatus capable of storing, sometimes permanently, machine-implementable instructions, data, and/or information, in analog and/or digital format. Examples include at least one non-volatile memory, volatile memory, register, relay, switch, Random Access Memory, RAM, Read Only Memory, ROM, flash memory, magnetic media, hard disk, floppy disk, magnetic tape, optical media, optical disk, compact disk, CD, digital versatile disk, DVD, and/or raid array, etc. The memory device can be coupled to a processor and/or can store and provide instructions adapted to be executed by processor, such as according to an embodiment disclosed herein.

memory device—an apparatus capable of storing, sometimes permanently, machine-implementable instructions, data, and/or information, in analog and/or digital format. Examples include at least one non-volatile memory, volatile memory, register, relay, switch, Random Access Memory, RAM, Read Only Memory, ROM, flash memory, magnetic media, hard disk, floppy disk, magnetic tape, optical media, optical disk, compact disk, CD, digital versatile disk, DVD, and/or raid array, etc. The memory device can be coupled to a processor and/or can store and provide instructions adapted to be executed by processor, such as according to an embodiment disclosed herein.

method—one or more acts that are performed upon subject matter to be transformed to a different state or thing and/or are tied to a particular apparatus, said one or more acts not a fundamental principal and not preempting all uses of a fundamental principal.

middle—a CTO distance within a range of approximately 0.7 to approximately 1.3 meters.

more—a quantifier meaning greater in size, amount, extent, and/or degree.

movement—an act or instance of moving; and/or a change in position from one location to another.

muscle—a contractile organ consisting of a special bundle of muscle tissue, which moves a particular bone, part, or substance of the body.

nanowire—a structure having a thickness or diameter constrained to tens of nanometers or less and an aspect ratio (length-to-width ratio) of 1000 or more.

near—a CTO distance of less than approximately 0.2 meters.

network—a communicatively coupled plurality of nodes, communication devices, and/or information devices. Via a network, such nodes and/or devices can be linked, such as via various wireline and/or wireless media, such as cables, telephone lines, power lines, optical fibers, radio waves, and/or light beams, etc., to share resources (such as printers and/or memory devices), exchange files, and/or allow electronic communications therebetween. A network can be and/or can utilize any of a wide variety of sub-networks and/or protocols, such as a circuit switched, public-switched, packet switched, connection-less, wireless, virtual, radio, data, telephone, twisted pair, POTS, non-POTS, DSL, cellular, telecommunications, video distribution, cable, radio, terrestrial, microwave, broadcast, satellite, broadband, corporate, global, national, regional, wide area, backbone, packet-switched TCP/IP, IEEE 802.03, Ethernet, Fast Ethernet, Token Ring, local area, wide area, IP, public Internet, intranet, private, ATM, Ultra Wide Band (UWB), Wi-Fi, BlueTooth, Airport, IEEE 802.11, IEEE 802.11a, IEEE 802.11b, IEEE 802.11g, X-10, electrical power, 3G, 4G, multi-domain, and/or multi-zone sub-network and/or protocol, one or more Internet service providers, one or more network interfaces, and/or one or more information devices, such as a switch, router, and/or gateway not directly connected to a local area network, etc., and/or any equivalents thereof.

network interface—any physical and/or logical device, system, and/or process capable of coupling an information device to a network. Exemplary network interfaces comprise a telephone, cellular phone, cellular modem, telephone data modem, fax modem, wireless transceiver, communications port, Ethernet card, cable modem, digital subscriber line interface, bridge, hub, router, or other similar device, software to manage such a device, and/or software to provide a function of such a device.

non-overlapping—not extending over or covering a part of object—a discrete thing that is real, perceptible, and tangible.

offset—in a location near to but distinguishable from a given point or area.

one—being or amounting to a single unit, individual, and/or entire thing, item, and/or object.

only—substantially without anything further.

ophthalmic—of and/or relating to the eye.

operate—to perform a function and/or to work.

opposing—opposite; against; being the other of two complementary or mutually exclusive things; placed or located opposite, in contrast, in counterbalance, and/or across from something else and/or from each other.

optical—of or relating to light, sight, and/or a visual representation.

overlap—to extend over and cover a part of packet—a generic term for a bundle of data organized in a specific way for transmission, such as within and/or across a network, such as a digital packet-switching network, and comprising the data to be transmitted and certain control information, such as a destination address.

perceptible—capable of being perceived by the human senses.

perpendicular—intersecting at or forming substantially right angles;

and/or substantially at a right angle with respect to an axis.

phase—a relationship in time between successive states and/or cycles of an oscillating and/or repeating system (such as an alternating electric current, one or more light waves, and/or a sound wave) and: a fixed reference point; the states of another system; and/or the cycles of another system.

photograph—(n) an image created by collecting and focusing reflected electromagnetic radiation. The most common photographs are those created of reflected visible wavelengths, producing permanent records of what the human eye can see. (v) to record an image.

photolithography—a process whereby metallic foils, fluidic circuits, and/or printed circuits can be created by exposing a photosensitive substrate to a pattern, such as a predesigned structural pattern and/or a circuit pattern, and chemically etching away either the exposed or unexposed portion of the substrate.

photon—a particle representing a quantum of light and/or other electromagnetic radiation, the particle having zero rest mass and carrying energy proportional to the frequency of the radiation.

physical—tangible, real, and/or actual.

physical—tangible, real, and/or actual.

physically—existing, happening, occurring, acting, and/or operating in a manner that is tangible, real, and/or actual.

physically—existing, happening, occurring, acting, and/or operating in a manner that is tangible, real, and/or actual.

piezoelectric—the generation of electricity and/or of electric polarity in dielectric crystals subjected to mechanical stress, and/or the generation of stress in such crystals subjected to an applied voltage.

piston—a working member which has relative sliding sealing engagement with the encompassing wall of a cylinder type working chamber. The principal parts of a piston consist of an end face portion and a side wall portion which are defined as follows:

place—to put in a particular place and/or position.

plurality—the state of being plural and/or more than one.

point—(n.) a defined physical and/or logical location in at least a two-dimensional system and/or an element in a geometrically described set and/or a measurement or representation of a measurement having a time coordinate and a non-time coordinate. (v.) to indicate a position and/or direction of.

portion—a part, component, section, percentage, ratio, and/or quantity that is less than a larger whole. Can be visually, physically, and/or virtually distinguishable and/or non-distinguishable.

position—to put in place or position.

power—a measure of an ability of a vision system, eye, lens, and/or lens-assisted eye, to refract, magnify, separate, converge, and/or diverge; and/or a general term that may refer to any power such as effective, equivalent, dioptric, focal, refractive, surface, and/or vergence power; and/or energy, a measure of energy and/or work, and/or a rate at which work is done, expressed as the amount of work per unit time and commonly measured in units such as watt and horsepower.

pre-—a prefix that precedes an activity that has occurred beforehand and/or in advance.

predetermined—established in advance.

probability—a quantitative representation of a likelihood of an occurrence.

processor—a machine that utilizes hardware, firmware, and/or software and is physically adaptable to perform, via Boolean logic operating on a plurality of logic gates that form particular physical circuits, a specific task defined by a set of machine-implementable instructions. A processor can utilize mechanical, pneumatic, hydraulic, electrical, magnetic, optical, informational, chemical, and/or biological principles, mechanisms, adaptations, signals, inputs, and/or outputs to perform the task(s). In certain embodiments, a processor can act upon information by manipulating, analyzing, modifying, and/or converting it, transmitting the information for use by machine-implementable instructions and/or an information device, and/or routing the information to an output device. A processor can function as a central processing unit, local controller, remote controller, parallel controller, and/or distributed controller, etc. Unless stated otherwise, the processor can be a general-purpose device, such as a microcontroller and/or a microprocessor, such the Pentium family of microprocessor manufactured by the Intel Corporation of Santa Clara, Calif. In certain embodiments, the processor can be dedicated purpose device, such as an Application Specific Integrated Circuit (ASIC) or a Field Programmable Gate Array (FPGA) that has been designed to implement in its hardware and/or firmware at least a part of an embodiment disclosed herein. A processor can reside on and use the capabilities of a controller.

programmatically—of, relating to, or having a program and/or instructions.

project—to calculate, estimate, or predict.

provide—to furnish, supply, give, and/or make available.

provoke—to bring about, cause, elicit, and/or effect.

proximity—the state, quality, sense, and/or fact of being near and/or next;

the closeness of one thing to another.

radial—pertaining to that which radiates from and/or converges to a common center and/or has or is characterized by parts so arranged or so radiating.

receive—to get as a signal, take, acquire, and/or obtain.

receiver—an apparatus adapted to accept, receive, and/or capture: data provided by a communications system and/or a signal transmitted by a transmitter.

recommend—to suggest, praise, commend, and/or endorse.

record—(v) to gather, capture, store, and/or preserve information on a tangible medium.

reduce—to make and/or become lesser and/or smaller.

render—to, e.g., physically, chemically, biologically, electronically, electrically, magnetically, optically, acoustically, fluidically, and/or mechanically, etc., transform information into a form perceptible to a human as, for example, data, commands, text, graphics, audio, video, animation, and/or hyperlinks, etc., such as via a visual, audio, and/or haptic, etc., means and/or depiction, such as via a display, monitor, electric paper, ocular implant, cochlear implant, speaker, vibrator, shaker, force-feedback device, stylus, joystick, steering wheel, glove, blower, heater, cooler, pin array, tactile touchscreen, etc.

repeatedly—again and again; repetitively.

request—to express a desire for and/or ask for.

resistor—a two-terminal electronic component that opposes an electric current by producing a voltage drop between the two terminals in accordance with Ohm's law.

resolution—a degree of sharpness of an image.

ring—a substantially toroidal object that can be imagined as having been generated by rotating a closed loop (e.g., ellipse, circle, irregular curve, polygon, etc.) about a fixed line external to the loop.

scene—a place where action occurs and/or where an object of interest is present; something seen by a viewer; and/or a view and/or prospect.

second—an element following a first element in a set.

select—to make a choice or selection from alternatives.

send—to convey, dispatch, communicate, and/or transmit.

sense—to detect or perceive automatically.

sensor—a device adapted to automatically sense, perceive, detect, and/or measure a physical property (e.g., pressure, temperature, flow, mass, heat, light, sound, humidity, proximity, position, velocity, vibration, loudness, voltage, current, capacitance, resistance, inductance, magnetic flux, and/or electro-magnetic radiation, etc.) and convert that physical quantity into a signal. Examples include position sensors, proximity switches, stain gages, photo sensors, thermocouples, level indicating devices, speed sensors, accelerometers, electrical voltage indicators, electrical current indicators, on/off indicators, and/or flowmeters, etc.

sensor—a device adapted to automatically sense, perceive, detect, and/or measure a physical property (e.g., pressure, temperature, flow, mass, heat, light, sound, humidity, proximity, position, velocity, vibration, loudness, voltage, current, capacitance, resistance, inductance, magnetic flux, and/or electro-magnetic radiation, etc.) and convert that physical quantity into a signal. Examples include position sensors, proximity switches, stain gages, photo sensors, thermocouples, level indicating devices, speed sensors, accelerometers, electrical voltage indicators, electrical current indicators, on/off indicators, and/or flowmeters, etc.

separated—not touching and/or spaced apart by something.

server—an information device and/or a process running thereon, that is adapted to be communicatively coupled to a network and that is adapted to provide at least one service for at least one client, i.e., for at least one other information device communicatively coupled to the network and/or for at least one process running on another information device communicatively coupled to the network. One example is a file server, which has a local drive and services requests from remote clients to read, write, and/or manage files on that drive. Another example is an e-mail server, which provides at least one program that accepts, temporarily stores, relays, and/or delivers e-mail messages. Still another example is a database server, which processes database queries. Yet another example is a device server, which provides networked and/or programmable: access to, and/or monitoring, management, and/or control of, shared physical resources and/or devices, such as information devices, printers, modems, scanners, projectors, displays, lights, cameras, security equipment, proximity readers, card readers, kiosks, POS/retail equipment, phone systems, residential equipment, HVAC equipment, medical equipment, laboratory equipment, industrial equipment, machine tools, pumps, fans, motor drives, scales, programmable logic controllers, sensors, data collectors, actuators, alarms, annunciators, and/or input/output devices, etc.

set—a related plurality.

sharpness—acuteness and/or distinctness.

signal—(v) to communicate; (n) one or more automatically detectable variations in a physical variable, such as a pneumatic, hydraulic, acoustic, fluidic, mechanical, electrical, magnetic, optical, chemical, and/or biological variable, such as power, energy, pressure, flowrate, viscosity, density, torque, impact, force, frequency, phase, voltage, current, resistance, magnetomotive force, magnetic field intensity, magnetic field flux, magnetic flux density, reluctance, permeability, index of refraction, optical wavelength, polarization, reflectance, transmittance, phase shift, concentration, and/or temperature, etc., that can encode information, such as machine-implementable instructions for activities and/or one or more letters, words, characters, symbols, signal flags, visual displays, and/or special sounds, etc., having prearranged meaning. Depending on the context, a signal and/or the information encoded therein can be synchronous, asynchronous, hard real-time, soft real-time, non-real time, continuously generated, continuously varying, analog, discretely generated, discretely varying, quantized, digital, broadcast, multicast, unicast, transmitted, conveyed, received, continuously measured, discretely measured, processed, encoded, encrypted, multiplexed, modulated, spread, de-spread, demodulated, detected, de-multiplexed, decrypted, and/or decoded, etc.

solid angle—a three-dimensional angle, formed by three or more planes intersecting at a common point. Its magnitude is measured in steradians, a unitless measure. The corner of a room forms a solid angle, as does the apex of a cone; one can imagine an indefinite number of planes forming the smooth round surface of the cone all intersecting at the apex. Solid angles are commonly used in photometry.

special purpose computer—a computer and/or information device comprising a processor device having a plurality of logic gates, whereby at least a portion of those logic gates, via implementation of specific machine-implementable instructions by the processor, experience a change in at least one physical and measurable property, such as a voltage, current, charge, phase, pressure, weight, height, tension, level, gap, position, velocity, momentum, force, temperature, polarity, magnetic field, magnetic force, magnetic orientation, reflectivity, molecular linkage, molecular weight, etc., thereby directly tying the specific machine-implementable instructions to the logic gate's specific configuration and property(ies). In the context of an electronic computer, each such change in the logic gates creates a specific electrical circuit, thereby directly tying the specific machine-implementable instructions to that specific electrical circuit.

special purpose processor—a processor device, having a plurality of logic gates, whereby at least a portion of those logic gates, via implementation of specific machine-implementable instructions by the processor, experience a change in at least one physical and measurable property, such as a voltage, current, charge, phase, pressure, weight, height, tension, level, gap, position, velocity, momentum, force, temperature, polarity, magnetic field, magnetic force, magnetic orientation, reflectivity, molecular linkage, molecular weight, etc., thereby directly tying the specific machine-implementable instructions to the logic gate's specific configuration and property(ies). In the context of an electronic computer, each such change in the logic gates creates a specific electrical circuit, thereby directly tying the specific machine-implementable instructions to that specific electrical circuit.

spherical—of, relating to, and/or having a shape approximating that of a sphere.

spring—a flexible elastic object, such as a coil of wire, bent bar, coupled set of plates, washer, etc., that regains its original shape after being compressed or extended, is used to store mechanical energy, and is often made of hardened and tempered material, such as steel. Types of springs can include coil springs, helical springs, conical springs, torsion springs, tension springs, compression springs, leaf springs, V-springs, spiral springs, spring washers, gas springs, rubber bands, etc.

state—a qualitative and/or quantitative description of condition, and/or a condition of an entity at an identified time.

store—to place, hold, and/or retain data, typically in a memory.

storage device—a device adapted to store information, energy, and/or one or more physical things for subsequent use and/or retrieval.

strip—a relatively long piece, usually of substantially uniform width.

structure—something made up of a number of parts that are held and/or put together in a particular way.

substantially—to a great extent and/or degree.

substrate—an underlying material, region, base, stratum, course, lamina, coating, and/or sheet.

sufficiently—to a degree necessary to achieve a predetermined result.

support—to bear the weight of, especially from below.

surface—the outer boundary of an object and/or a material layer constituting and/or resembling such a boundary.

switch—(n.) a mechanical, electrical, and/or electronic device that opens and/or closes circuits, completes and/or breaks an electrical path, and/or selects paths and/or circuits; (v.) to: form, open, and/or close one or more circuits; form, complete, and/or break an electrical and/or informational path; alternate between electrically energizing and de-energizing; select a path and/or circuit from a plurality of available paths and/or circuits; and/or establish a connection between disparate transmission path segments in a network (or between networks); (n) a physical device, such as a mechanical, electrical, and/or electronic device, that is adapted to switch.

switch—(v) to: form, open, and/or close one or more circuits; form, complete, and/or break an electrical and/or informational path; select a path and/or circuit from a plurality of available paths and/or circuits; and/or establish a connection between disparate transmission path segments in a network (or between networks); (n) a physical device, such as a mechanical, electrical, and/or electronic device, that is adapted to switch.

switching speed—the time required to change from one CTO distance to another.

system—a collection of mechanisms, devices, machines, articles of manufacture, processes, data, and/or instructions, the collection designed to perform one or more specific functions.

transfer—(n) a transmission from one device, place, and/or state to another. (v) to convey from one device, place, and/or state to another.

transform—to change in measurable: form, appearance, nature, and/or character.

transmit—to send as a signal, provide, furnish, and/or supply.

transmitter—a device that generates and/or transmits a meaningful signal, often optically, chemically, acoustically, hydraulically, pneumatically, electrically, electronically, and/or via electromagnetic waves.

transparent—clear; characterized by conveying incident light without reflecting or absorbing a substantial portion of that light; and/or having the property of transmitting rays of light through its substance so that bodies situated beyond or behind can be distinctly seen.

unique—separate and distinct.

user—a person, organization, process, device, program, protocol, and/or system, such as a wearer, subscriber, customer, provider, server administrator, etc., that uses at least a portion of a device, system, process, method, and/or service described herein.

user interface—any device for rendering information to a user and/or requesting information from the user. A user interface includes at least one of textual, graphical, audio, video, animation, and/or haptic elements. A textual element can be provided, for example, by a printer, monitor, display, projector, etc. A graphical element can be provided, for example, via a monitor, display, projector, and/or visual indication device, such as a light, flag, beacon, etc. An audio element can be provided, for example, via a speaker, microphone, and/or other sound generating and/or receiving device. A video element or animation element can be provided, for example, via a monitor, display, projector, and/or other visual device. A haptic element can be provided, for example, via a very low frequency speaker, vibrator, tactile stimulator, tactile pad, simulator, keyboard, keypad, mouse, trackball, joystick, gamepad, wheel, touchpad, touch panel, pointing device, and/or other haptic device, etc. A user interface can include one or more textual elements such as, for example, one or more letters, number, symbols, etc. A user interface can include one or more graphical elements such as, for example, an image, photograph, drawing, icon, window, title bar, panel, sheet, tab, drawer, matrix, table, form, calendar, outline view, frame, dialog box, static text, text box, list, pick list, pop-up list, pull-down list, menu, tool bar, dock, check box, radio button, hyperlink, browser, button, control, palette, preview panel, color wheel, dial, slider, scroll bar, cursor, status bar, stepper, and/or progress indicator, etc. A textual and/or graphical element can be used for selecting, programming, adjusting, changing, specifying, etc. an appearance, background color, background style, border style, border thickness, foreground color, font, font style, font size, alignment, line spacing, indent, maximum data length, validation, query, cursor type, pointer type, autosizing, position, and/or dimension, etc. A user interface can include one or more audio elements such as, for example, a volume control, pitch control, speed control, voice selector, and/or one or more elements for controlling audio play, speed, pause, fast forward, reverse, etc. A user interface can include one or more video elements such as, for example, elements controlling video play, speed, pause, fast forward, reverse, zoom-in, zoom-out, rotate, and/or tilt, etc. A user interface can include one or more animation elements such as, for example, elements controlling animation play, pause, fast forward, reverse, zoom-in, zoom-out, rotate, tilt, color, intensity, speed, frequency, appearance, etc. A user interface can include one or more haptic elements such as, for example, elements utilizing tactile stimulus, force, pressure, vibration, motion, displacement, temperature, etc.

valve—a device that regulates flow through a pipe and/or through an aperture by opening, closing, and/or obstructing a port and/or passageway.

variable—(n) a property, parameter, and/or characteristic capable of assuming any of an associated set of values. (adj) likely to change and/or vary; subject to variation; and/or changeable.

variable-focus—having the quality of adjustable focus in a single specified optic.

vary—to change, alter, and/or modify one or more characteristics and/or attributes of via—by way of and/or utilizing.

visual—able to be seen by the eye; visible.

voltage—(a.k.a., "potential difference" and "electro-motive force" (EMF)) a difference in electrical potential between any two conductors of an electrical circuit and/or a quantity, expressed as a signed number of Volts (V), and measured as a signed difference between two points in an electrical circuit which, when divided by the resistance in Ohms between those points, gives the current flowing between those points in Amperes, according to Ohm's Law.

wavefront—a surface containing points affected in substantially the same way by a wave at a substantially predetermined time.

weight—a value indicative of importance.

when—at a time and/or during the time at which.

wherein—in regard to which; and; and/or in addition to.

wireless—any communication technique that transmits a signal that does not require the use of a wire and/or guide connecting a transmitter and a receiver and/or utilizes electromagnetic waves emitted by an antenna (i.e., via an unguided medium), including such communication techniques as sonar, radio, cellular, cellular radio, digital cellular radio, ELF, LF, MF, HF, VHF, UHF, SHF, EHF, radar, microwave, satellite microwave, laser, infrared, etc., but excluding purely visual signaling, such as semaphore, smoke signals, sign language, etc., the communication technique having a baseband and/or carrier frequency ranging from about 1 Hz to about $2 \times 10^{14}$ Hz (about 200 teraHertz), including all values therebetween, such as for example, about 40 Hz, 6.010 kHz, 8.7 MHz, 4.518 GHz, 30 GHz, etc. and including all subranges therebetween, such as for example, from about 100 kHz to about 100 MHz, about 30 MHz to about 1 GHz, about 3 kHz to about 300 GHz, etc. Wireless communications can include analog and/or digital data, signals, and/or transmissions. Wireless communication can be via any of a plurality of protocols such as, for example, cellular CDMA, TDMA, GSM, GPRS, UMTS, W-CDMA, CDMA2000, TD-CDMA, 802.11a, 802.11b, 802.11g, 802.15.1, 802.15.4, 802.16, and/or Bluetooth, etc.

with—accompanied by.

within—inside the limits of.

worn—donned by a wearer.

zonule—a ring of fibrous strands connecting the ciliary body with the crystalline lens of the eye.

Note

Various substantially and specifically practical and useful exemplary embodiments are described herein, textually and/or graphically, including the best mode, if any, known to the inventor(s), for implementing the described subject matter by persons having ordinary skill in the art. Any of numerous possible variations (e.g., modifications, augmentations, embellishments, refinements, and/or enhancements, etc.), details (e.g., species, aspects, nuances, and/or elaborations, etc.), and/or equivalents (e.g., substitutions, replacements, combinations, and/or alternatives, etc.) of one or more embodiments described herein might become apparent upon reading this document to a person having ordinary skill in the art, relying upon his/her expertise and/or knowledge of the entirety of the art and without exercising undue experimentation. The inventor(s) expects skilled artisans to implement such variations, details, and/or equivalents as appropriate, and the inventor(s) therefore intends for the described subject matter to be practiced other than as specifically described herein. Accordingly, as permitted by law, the described subject matter includes and covers all variations, details, and equivalents of that described subject matter. Moreover, as permitted by law, every combination of the herein described characteristics, functions, activities, substances, and/or structural elements, and all possible variations, details, and equivalents thereof, is encompassed by the described subject matter unless otherwise clearly indicated herein, clearly and specifically disclaimed, or otherwise clearly contradicted by context.

The use of any and all examples, or exemplary language (e.g., "such as") provided herein, is intended merely to better illuminate one or more embodiments and does not pose a limitation on the scope of any described subject matter unless otherwise stated. No language herein should be construed as indicating any described subject matter as essential to the practice of the described subject matter.

Thus, regardless of the content of any portion (e.g., title, field, background, summary, description, abstract, drawing figure, etc.) of this document, unless clearly specified to the contrary, such as via explicit definition, assertion, or argument, or clearly contradicted by context, with respect to any claim, whether of this document and/or any claim of any document claiming priority hereto, and whether originally presented or otherwise:

there is no requirement for the inclusion of any particular described characteristic, function, activity, substance, or structural element, for any particular sequence of activities, for any particular combination of substances, or for any particular interrelationship of elements;

no described characteristic, function, activity, substance, or structural element is "essential";

any two or more described substances can be mixed, combined, reacted, separated, and/or segregated;

any described characteristics, functions, activities, substances, and/or structural elements can be integrated, segregated, and/or duplicated;

any described activity can be performed manually, semi-automatically, and/or automatically;

any described activity can be repeated, any activity can be performed by multiple entities, and/or any activity can be performed in multiple jurisdictions; and any described characteristic, function, activity, substance, and/or structural element can be specifically excluded, the sequence of activities can vary, and/or the interrelationship of structural elements can vary.

The use of the terms "a", "an", "said", "the", and/or similar referents in the context of describing various embodiments (especially in the context of any claims presented herein or in any document claiming priority hereto) are to be construed to cover both the singular and the plural, unless otherwise indicated herein or clearly contradicted by context.

The terms "comprising," "having," "including," and "containing" are to be construed as open-ended terms (i.e., meaning "including, but not limited to,") unless otherwise noted.

When any number or range is described herein, unless clearly stated otherwise, that number or range is approximate. Recitation of ranges of values herein are merely intended to serve as a shorthand method of referring individually to each separate value falling within the range, unless otherwise indicated herein, and each separate value and each separate subrange defined by such separate values is incorporated into and clearly implied as being presented within the specification as if it were individually recited herein. For example, if a range of 1 to 10 is described, even implicitly, unless otherwise stated, that range necessarily includes all values therebetween, such as for example, 1.1, 2.5, 3.335, 5, 6.179, 8.9999, etc., and includes all subranges therebetween, such as for example, 1 to 3.65, 2.8 to 8.14, 1.93 to 9, etc.

When any phrase (i.e., one or more words) described herein or appearing in a claim is followed by a drawing element number, that drawing element number is exemplary and non-limiting on the description and claim scope.

No claim of this document or any document claiming priority hereto is intended to invoke paragraph six of 35 USC 112 unless the precise phrase "means for" is followed by a gerund.

Any information in any material (e.g., a United States patent, United States patent application, book, article, etc.) that has been incorporated by reference herein, is incorporated by reference herein in its entirety to its fullest enabling extent permitted by law yet only to the extent that no conflict exists between such information and the other statements and drawings set forth herein. In the event of such conflict, including a conflict that would render invalid any claim herein or seeking priority hereto, then any such conflicting information in such material is specifically not incorporated by reference herein.

Within this document, and during prosecution of any patent application related hereto (including any patent application claiming priority hereto) any reference to any claimed subject matter is intended to reference the precise language of the then-pending claimed subject matter at that particular point in time only.

Accordingly, every portion (e.g., title, field, background, summary, description, abstract, drawing figure, etc.) of this document, and any provided definitions of the phrases used herein, is to be regarded as illustrative in nature, and not as restrictive. The scope of subject matter protected by any claim of any patent that issues based on this document is defined and limited only by the precise language of that claim (and all legal equivalents thereof) and any provided definition of any phrase used in that claim, as informed by the context of this document.

What is claimed is:

1. A method of actuating a bi-stable electro-active lens that retains its last optical power setting when electrical power is removed from the electro-active lens, the method comprising:

causing an optical state of the electro-active lens to be retained when the electrical power is removed from the electro-active lens;

increasing an optical power of the electro-active lens in response to detecting a first predetermined movement of an entirety of a transmitter with respect to the electro-active lens, the transmitter attached to a hand of a wearer of the electro-active lens, the first predetermined movement indicated by a first signal sent by the transmitter; and decreasing the optical power of the electro-active lens in response to detecting a second predetermined movement of the entirety of the transmitter with respect to the electro-active lens, the second predetermined movement indicated by a second signal sent by the transmitter.

2. The method of claim 1, wherein:
the first predetermined movement of the transmitter is caused by moving a first finger of the hand of the wearer toward the electro-active lens.

3. The method of claim 1, wherein:
the second predetermined movement of the transmitter is caused by moving a second finger of the hand of the wearer toward the electro-active lens.

4. The method of claim 1, further comprising:
actuating the electro-active lens in response to detecting a predetermined motion of a combination of fingers of the hand of the wearer.

5. A method of actuating a bi-stable electro-active lens that retains its last optical power setting when electrical power is removed from the electro-active lens, the method comprising:
causing an optical state of the electro-active lens to be retained when the electrical power is removed from the electro-active lens;
increasing an optical power of an electro-active lens in response to detecting a first movement of a hand of a wearer of the electro-active lens, the first movement causing an entire transmitter to move with respect to the electro-active lens; and
decreasing the optical power of the electro-active lens in response to detecting a second movement of the hand of the wearer of the electro-active lens, the second movement causing the entire transmitter to move with respect to the electro-active lens.

* * * * *